United States Patent
Smith

(10) Patent No.: US 11,654,040 B2
(45) Date of Patent: May 23, 2023

(54) VERTICAL EXTENSION NECK BRACE

(71) Applicant: PAINTSMITH DECOR LTD., Edmonton (CA)

(72) Inventor: Amanda Smith, Edmonton (CA)

(73) Assignee: Paintsmith Decor Ltd., Edmonton (CA)

( * ) Notice: Subject to any disclaimer, the term of this patent is extended or adjusted under 35 U.S.C. 154(b) by 479 days.

(21) Appl. No.: 16/840,646

(22) Filed: Apr. 6, 2020

(65) Prior Publication Data

US 2021/0186737 A1 Jun. 24, 2021

Related U.S. Application Data

(60) Provisional application No. 62/952,706, filed on Dec. 23, 2019.

(51) Int. Cl.
*A61F 5/058* (2006.01)

(52) U.S. Cl.
CPC ................. *A61F 5/05883* (2013.01)

(58) Field of Classification Search
CPC ........ A61F 5/05883; A61F 5/058; A61F 5/05; A61F 5/04; A61F 5/01; A61F 5/00; A61F 5/05833; A61F 5/05816; A61F 5/055
See application file for complete search history.

(56) References Cited

U.S. PATENT DOCUMENTS

| | | | | |
|---|---|---|---|---|
| 2,904,040 A | * | 9/1959 | Hale | A61F 5/055 602/18 |
| 3,900,896 A | | 8/1975 | Ackerman | |
| 4,643,174 A | * | 2/1987 | Horiuchi | A61F 5/055 602/18 |
| 5,248,293 A | * | 9/1993 | Hubbard | A61F 5/055 602/17 |
| 5,409,450 A | * | 4/1995 | Donelson | A61F 5/055 602/17 |
| 6,308,345 B1 | * | 10/2001 | Williams, Jr. | A41D 13/0512 602/17 |
| 7,618,385 B2 | | 11/2009 | Poole | |
| 7,892,193 B2 | * | 2/2011 | Marchetto | A61F 5/055 602/18 |
| 8,834,394 B2 | | 9/2014 | Ghajar | |
| 10,561,866 B1 | * | 2/2020 | Hinnant | A62B 35/0025 |
| 2001/0027283 A1 | | 10/2001 | Poole | |
| 2003/0050582 A1 | | 3/2003 | Poole | |
| 2005/0283884 A1 | * | 12/2005 | Poole | A41D 13/05 2/468 |
| 2010/0204628 A1 | * | 8/2010 | Ghajar | A61F 5/055 602/18 |

(Continued)

FOREIGN PATENT DOCUMENTS

WO WO-0078254 A1 * 12/2000 ............. A41D 13/05
WO WO-2015061663 A1 * 4/2015 ......... A41D 13/0512

*Primary Examiner* — Tarla R Patel
(74) *Attorney, Agent, or Firm* — Bennett Jones LLP

(57) ABSTRACT

A neck stabilizing device for supporting a user's neck in vertical extension, includes a harness configured to be worn on a user's torso and a neck bracing member having an elongated stem for attachment to the harness, and a support portion configured to contact the base of the user's skull. The neck bracing member is shaped to follow the anterior and posterior curvature of the user's spine, and is flexibly resilient to allow for and resist neck extension.

10 Claims, 5 Drawing Sheets

(56) References Cited

U.S. PATENT DOCUMENTS

| | | | |
|---|---|---|---|
| 2014/0020163 A1* | 1/2014 | Stiles | A42B 3/0473 2/468 |
| 2016/0089554 A1* | 3/2016 | Perner | A62B 35/0025 182/3 |
| 2020/0054475 A1* | 2/2020 | Deetsch | A61F 5/055 |

* cited by examiner

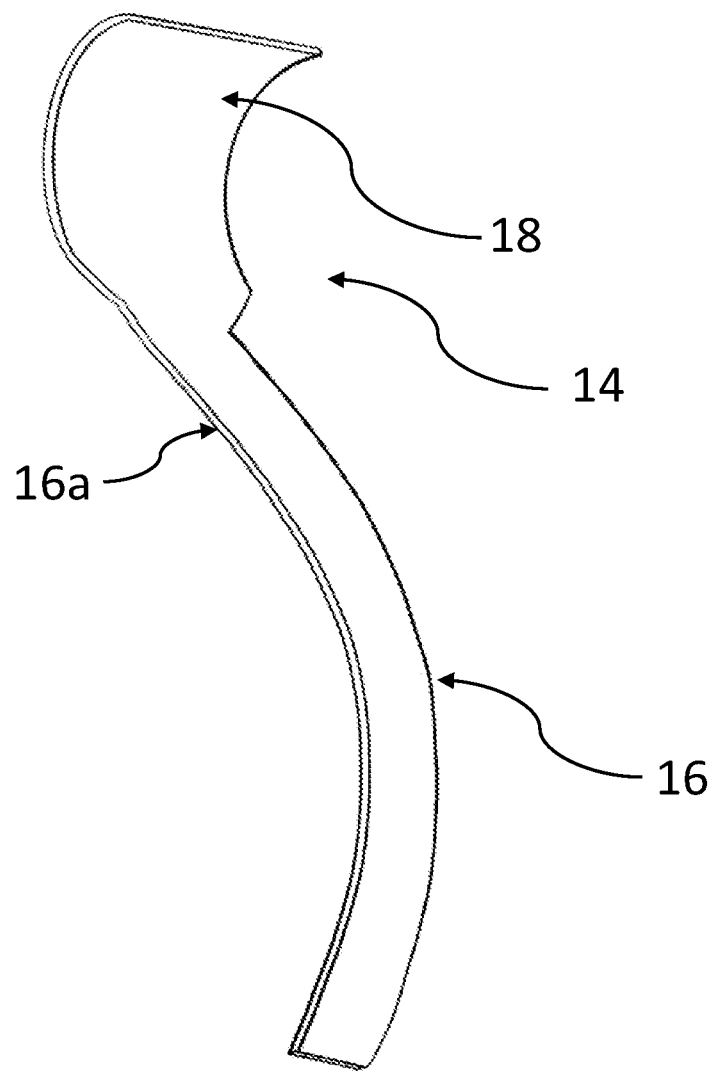

VERTICAL EXTENSION NECK BRACE

FIELD OF THE INVENTION

The present invention relates to a device for supporting and stabilizing a user's neck and/or head during work requiring neck extension.

BACKGROUND

Certain work requires a worker to look upwards. In doing so, the worker will put his/her neck into extension, which may be uncomfortable and/or harmful. As used herein, "extension" refers to backwards bending movement of the neck such that the subject's head moves backwards, looking upwards. Hyperextension can result in serious injury.

Certain work routinely requires a worker to look straight upwards with both hands held above the head, often holding tools and equipment and wearing protective safety devices. Examples of trades where workers are required to look upwards for long periods of time include but are not limited to: construction workers, welders, oilfield workers, ironworkers, pipefitters, painters, drywall installers and tapers, framers, electricians, plumbers, mechanics, window washers, eaves trough technicians, arborists, and warehouse workers.

Neck and head braces are known but invariably involve a head support member, which limits range of motion of the user's head. These devices are unsatisfactory from many different aspects.

There is a need in the art for a device which is comfortable, supportive and may be worn with safety gear that is often required by workers who may desire to wear such devices.

SUMMARY OF THE INVENTION

In one aspect, the invention comprises a neck brace comprising:
(a) a harness configured to be worn on the torso of a user;
(b) a neck bracing member comprising a stem which engages the harness and a lower portion and a upper portion, the member curved anteriorly in the lower portion and then posteriorly in the upper portion, thus achieving a concave shape.

The neck bracing member is preferably resiliently flexible, and fashioned from a material such as a plastic, a composite, or a metal. The neck bracing member stem is preferably adjustably positionable in the harness to accommodate different user sizes, and/or may itself be of adjustable length.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 2 shows one embodiment of a neck bracing member.

DETAILED DESCRIPTION

Figure 1:
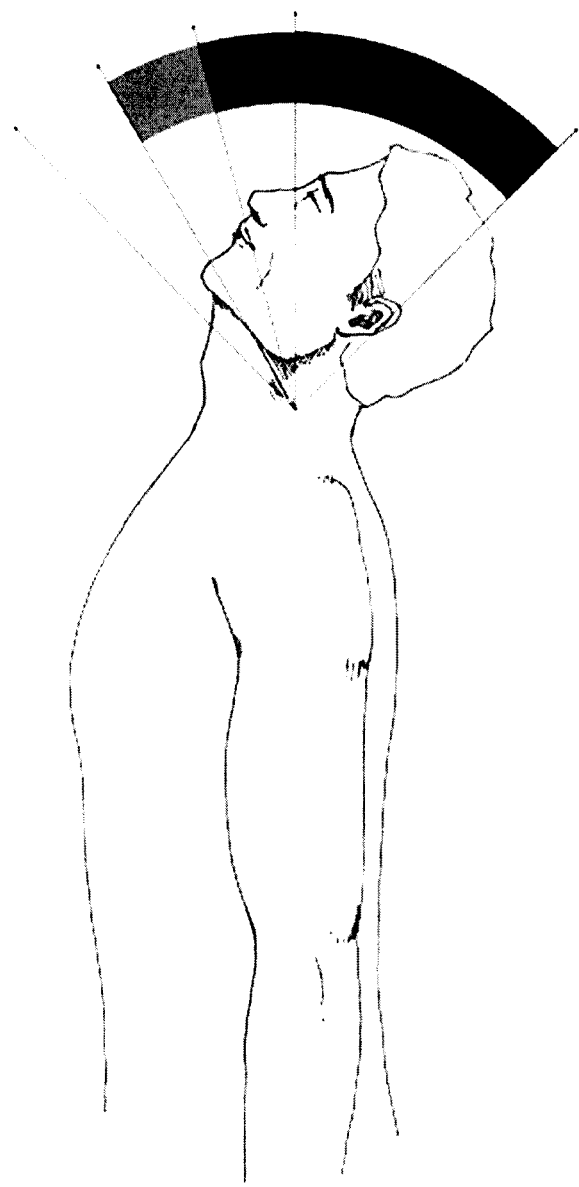
FIG. 1 shows the range of flexion/extension motion of a human head in the sagittal plane.

FIG. 1 shows typical human anatomy and demonstrates the danger zone of neck extension, where the head moves backwards in the sagittal plane. As may be seen, greater extension results in greater risk of injury. Many individuals performing overhead manual tasks place their neck into extension when looking upwards. If the neck extension is prolonged or extreme, fatigue and/or injury may occur.

Embodiments of this invention stabilizes and provides protection to the neck so that a user who is required to look up in vertical extension is less likely to suffer discomfort, pain or injury from muscle strain, vertebral issues, or pinched nerves caused by compression of the vertebrae. The present invention is configured to promote a healthy curvature of the spine and to maintain this spinal length even when the neck and head is in extension.

Figure 5A:
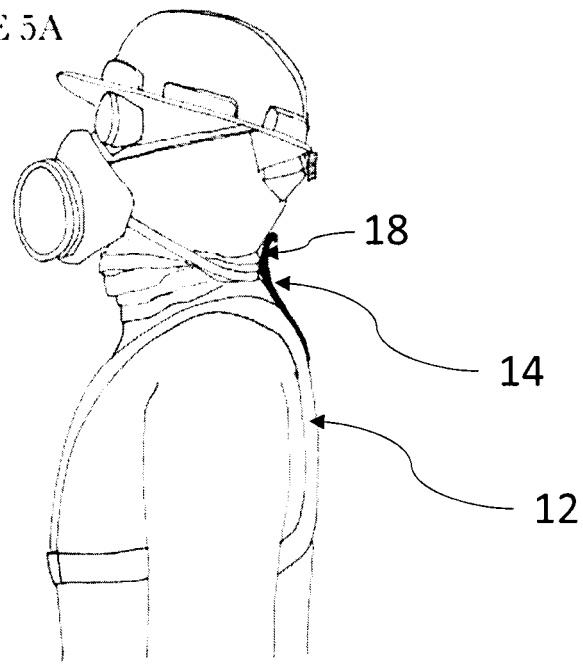
FIG. 5A shows a worker wearing one embodiment of the device together with a helmet, safety goggles and mask.

In some embodiments, the device (10) comprises a harness (12) configured to worn on a user's torso, and a neck bracing member (14) which extends upwards from the harness and follows the contours of the neck when in a comfortable upright position (as shown in FIG. 5A). The neck bracing member (14) is resiliently flexible, or mounted to the harness in resilient manner, to permit but resist neck extension, thereby supporting a user's head comfortably when the user is looking up and performing above-the-head work, thereby reducing strain on the neck muscles and/or compression of the neck vertebrae.

One embodiment of the neck bracing member is shown in FIG. 2, and comprises a stem (16) which cooperates with the harness (12) to hold the neck bracing member (14) securely in place. A support member (18) preferably comprises an expanded portion which has a slight posterior curve, as is shown in FIG. 2. An upper part (16a) of the stem (16) has a slight anterior curve so as to follow a user's neck curve. Preferably, the stem (16) and harness (12) cooperate in an adjustable manner, such that the stem may be adjustable vertically to accommodate user size and physique differences.

Figure 3A:
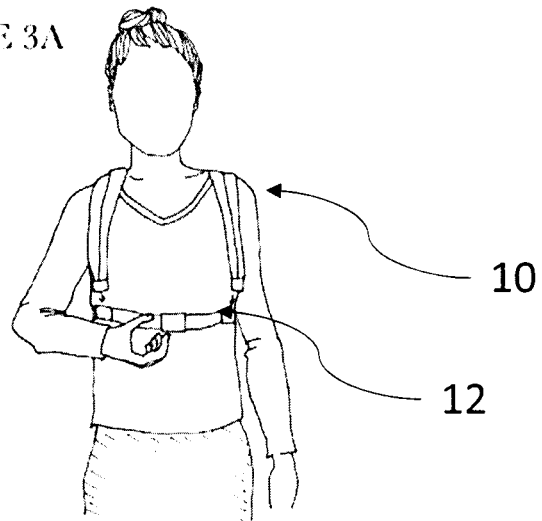
FIG. 3A shows a front view of a harness worn by a user.
Figure 3B:
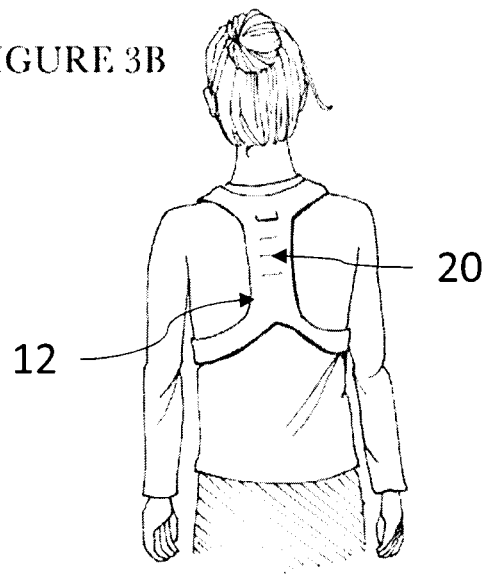
FIG. 3B shows a rear view of the same harness.
Figure 3C:
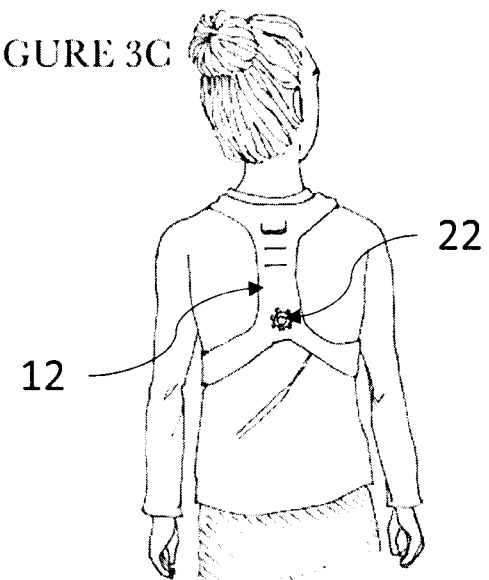
FIG. 3C shows an alternative embodiment of the harness.

One embodiment of a harness (12) is shown in FIGS. 3A, 3B and 3C. The harness (12) is preferably a fabric harness (12) comprising one or more sturdily sewn pockets (20) on the back to receive insertion of the stem (16), and for ease of positioning and adjusting the stem (16). In one embodiment, the harness may comprise a plurality of laddered pockets (20). It is preferred to position the neck bracing member (14) such that an upper portion of the support member (18) is positioned slightly above the user's first cervical vertebra (C1), which is positioned at the base of the skull. The C1 vertebrae is positioned immediately below the skull, and thus the neck bracing member (14) may be positioned to allow the base of the skull to contact an upper portion of the support member (18).

A rotary dial mechanism (22) which comprises a gear wheel which cooperates with teeth or pawls (not shown) on the stem (16) may be provided to allow for fine adjustment of the position of the stem within the harness. In alternative embodiments, the neck bracing member may be configured to be of adjustable length by having an adjustable mechanism to be secured to the harness, such as any suitable belt or strap mechanism allowing for adjustable length. Alternatively, the stem itself may have an adjustable length, such as by being fashioned from two pieces which slide relative to each other.

The stem (16) has an upper portion (16a) which curves anteriorly ie. towards the user's front, and the support portion (18) which curves posteriorly. The device thus cradles the user's neck in a concave shape when the user's head is in a neutral position, as may be seen in FIG. 4.

Figure 4:
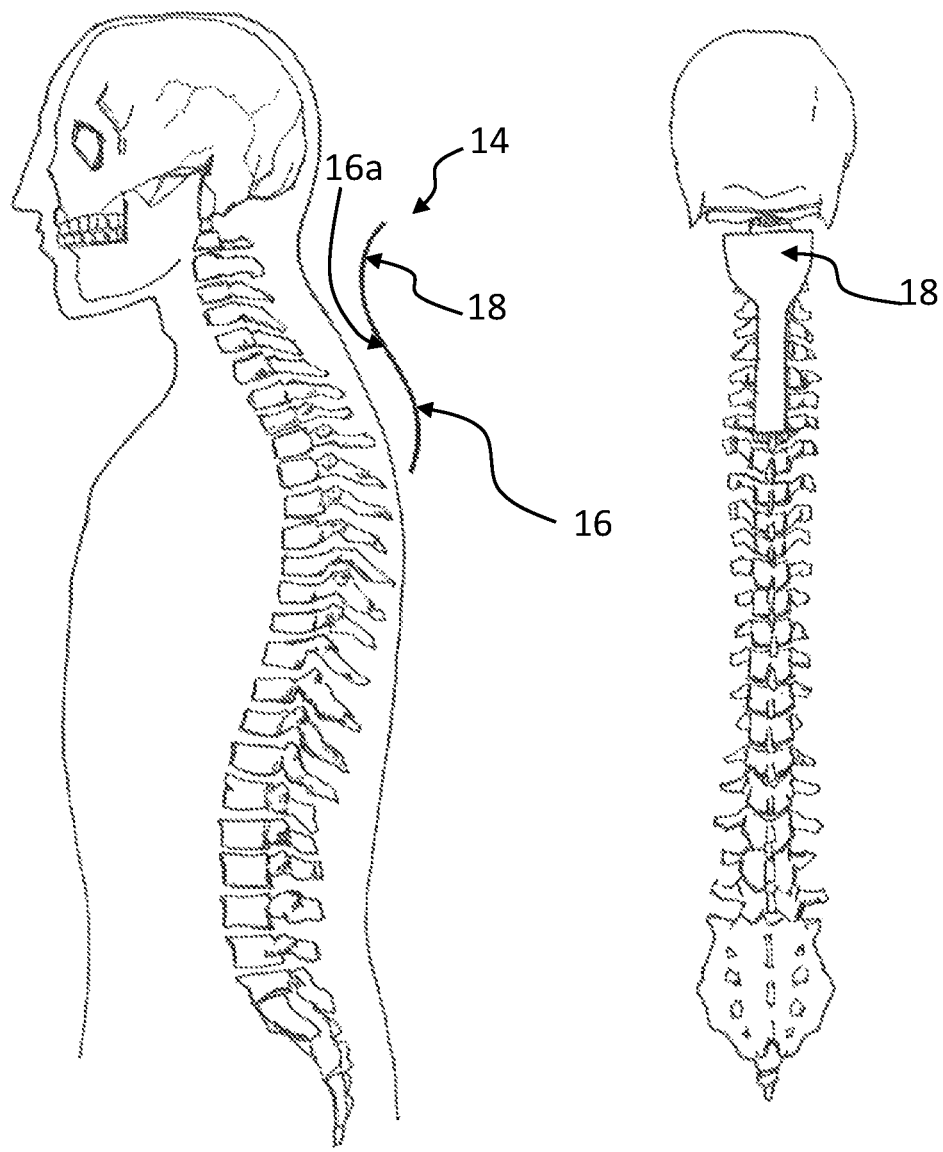
FIG. 4 shows a schematic view of the neck bracing member in relation to a human spine and skull.

In some embodiments, the support member (18) may widen from bottom to top, as is shown in the rear view of FIG. 4. This configuration may allow for some limited side-to-side motion of the head, while maintaining supportive and stabilizing contact with the neck.

In preferred embodiments, the neck bracing member is resiliently flexible and may be fashioned from any suitable material with sufficient strength and flexibility. Many plastics, composite materials, or metals may be suitable. In one preferred embodiment, the neck bracing member may be comprised of carbon fiber composite, chosen for its strength, resiliency, and light weight.

In preferred embodiments, the neck bracing member comprises substantially smooth surfaces and edges, to mitigate the possibility of catching on something or scratching a user. The neck bracing member may be covered with a fabric or other material which comfortably contacts the skin.

Figure 5B:
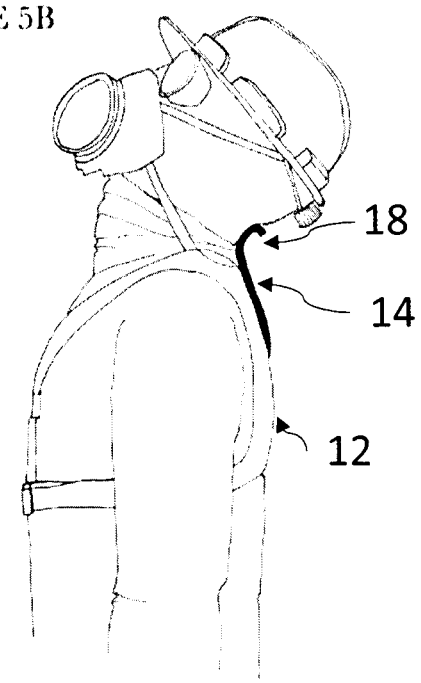
FIG. 5B shows the same worker with her neck in extension.

As may be seen in FIGS. 5A and 5B, because the upper part of the support portion (18) is positioned at or just above the position of the C1 vertebra, it allows wearing of safety equipment such as a mask, goggles, respirator, hard hat, or the like. Additionally, it allows comfortable use by individuals who have hair pony tails.

DEFINITIONS AND INTERPRETATION

The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. Embodiments were chosen and described in order to best explain the principles of the invention and the practical application, and to enable others of ordinary skill in the art to understand the invention for various embodiments with various modifications as are suited to the particular use contemplated.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described. In other words, any element or feature may be combined with any other element or feature in different embodiments, unless there is an obvious or inherent incompatibility between the two, or it is specifically excluded.

The invention claimed is:

1. A device for supporting a user's neck in extension, comprising:
    (a) a harness configured to be worn on the user's torso; and
    (b) a neck bracing member comprising a vertical elongated stem for attachment to the harness, and a support portion configured to contact a base of the user's skull, wherein the neck bracing member is flexibly resilient, and wherein an upper portion of the vertical elongated stem is curved anteriorly so as to follow the user's neck curve, and the support portion is curved posteriorly wherein the upper portion of the support portion is configured to be positioned at or above the user's C1 vertebrae, when the harness is worn on the user's torso.

2. The device of claim 1 wherein the device is adjustable to vary a height of the support portion.

3. The device of claim 2 wherein the harness comprises a vertically laddered series of openings for receiving the elongated stem such that the height of the support portion may be varied.

4. The device of claim 3 wherein the harness comprise a plurality of pockets, wherein each of the pockets defines a different one of the openings for receiving the elongated stem.

5. The device of claim 2 wherein the elongated stem itself is of adjustable length by being formed from two pieces that slide relative to each other.

6. The device of claim 2 wherein the device further comprises a rotary dial mechanism comprising a gear wheel that cooperates with teeth or pawls on the stem to allow for fine adjustment of a position of the elongated stem relative to the harness.

7. The device of claim 1 wherein the neck bracing member comprises a carbon fiber composite material.

8. The device of claim 1 wherein the support portion widens from bottom to top.

9. The device of claim 1 wherein the neck bracing member is configured to contact the user's neck, when the harness is worn on the user's torso.

10. The device of claim 1 wherein the neck bracing member is covered with a fabric.

* * * * *